(12) United States Patent
Eger

(10) Patent No.: US 7,605,184 B2
(45) Date of Patent: Oct. 20, 2009

(54) METHOD OF ANESTHESIA

(76) Inventor: Edmond Eger, 1895 Mountain View Dr., Tiburon, CA (US) 94920

( * ) Notice: Subject to any disclaimer, the term of this patent is extended or adjusted under 35 U.S.C. 154(b) by 138 days.

(21) Appl. No.: 12/017,814

(22) Filed: Jan. 22, 2008

(65) Prior Publication Data

US 2009/0183736 A1  Jul. 23, 2009

(51) Int. Cl.
*A61K 31/08* (2006.01)
*A61K 33/08* (2006.01)
*A61K 33/01* (2006.01)
(52) U.S. Cl. .................. 514/722; 424/693; 424/700
(58) Field of Classification Search .................. 514/722; 424/693, 700
See application file for complete search history.

(56) References Cited

U.S. PATENT DOCUMENTS 3,976,788 A    8/1976   Regan

OTHER PUBLICATIONS

Munson, Can. Anaesth. Soc. J. (1984) 31:642-645.
Murray et al., Anesthesiology (1999) 91:1342-1348.
Speers et al., J. Med. Chem. (1971) 14:593-595.

*Primary Examiner*—Raymond J Henley, III
(74) *Attorney, Agent, or Firm*—Morrison & Foerster LLP

(57) ABSTRACT

Inhaled anesthetics with otherwise desirable properties but which are too extensively degraded by passage through absorbents containing calcium hydroxide plus sodium hydroxide (such as soda lime) can be used as anesthetics by substituting absorbents containing calcium hydroxide but devoid of sodium hydroxide or containing minimal amounts of sodium hydroxide.

8 Claims, 4 Drawing Sheets

METHOD OF ANESTHESIA

TECHNICAL FIELD

The invention is in the field of inhaled anesthetics. More particularly, the invention concerns the use of anesthetics with desirable physiological properties that are virtually not degraded by specific carbon dioxide absorbents. Such absorbents contain calcium hydroxide without, or with but slight amounts of, monovalent bases.

BACKGROUND ART

The history of inhaled anesthetics dates back for more than a century and a half and was initiated with the use of diethyl ether, chloroform or nitrous oxide in the 1840's. While nitrous oxide is still used in some procedures, today's practitioners generally employ one of three fluorinated ethers—isoflurane of the formula $CHF_2$—O—$CHClCF_3$; desflurane of the formula $CHF_2$—O—$CHFCF_3$ which differs from isoflurane by replacement of the one chloro substituent with a fluoro, and sevoflurane of the formula $CH_2F$—O—$CH(CF_3)_2$. In general, the replacement of a chloro substituent with fluoro reduces the solubility of the anesthetic in blood (and thus accelerates recovery from anesthesia) and reduces toxicity. However, other disadvantages associated with desflurane as compared to isoflurane (decreased potency; greater cost of synthesis; greater pungency) somewhat mitigate the advantages of these properties. Sevoflurane also has minimal toxicity and the advantage of absent pungency, but it is significantly more soluble than desflurane and thus is associated with a slower recovery.

These anesthetics result from fairly recent efforts. During the decades of the 60's and 70's, Dr. Ross C. Terrell and his associates at Ohio Medical Products (now Baxter Healthcare Corp.) synthesized over 700 fluorinated compounds in a program for discovery of improved anesthetics. Isoflurane, desflurane and sevoflurane resulted from this effort. Wallin and co-workers at Travenol Laboratories in a similar program provided compounds that also resulted in the synthesis of sevoflurane.

An ideal anesthetic would have anesthetic properties at low concentrations in the lung, have low solubility in the blood, lack pungency, and would have minimal or no toxic or side effects such as enhancing blood pressure. Each of the commonly used inhaled anesthetics described above has a unique spectrum of properties that fall short of the ideal. The properties are described in Eger, II, E. I., et al., "The Pharmacology of Inhaled Anesthetics" (2002) published by Dannemiller Memorial Educational Foundation and incorporated herein by reference.

In standard procedures for administering inhaled fluorocarbon-based anesthetics, it is necessary, for economic reasons, to recycle the inhalant. Because the inhaled anesthetics in current use are difficult to synthesize, they are so expensive that simply administering them to a subject without recovering the exhaled gases from the subject and recycling them would be prohibitively expensive. Thus, a typical procedure for anesthesia by inhalation is shown in FIG. 1.

As shown, the delivered gas enters the cycling system and is transferred to a subject through a valve permitting inhalation. The exhaled gases from the subject are cycled through an expiratory valve to a carbon dioxide absorber which then cleanses the gases of carbon dioxide, permitting the unused previously-inhaled anesthetic to be recycled and again inhaled by the subject.

Traditionally, the carbon dioxide absorber has been a combination of hydroxides, including NaOH, KOH, $Ba(OH)_2$ and $Ca(OH)_2$. In most cases, 80% or more of the absorbent is $Ca(OH)_2$, but KOH and/or NaOH are generally added to accelerate the reaction with carbon dioxide. Further, the absorbent generally contains about 15% of water. The presence of water limits (e.g., sevoflurane) or prevents (e.g., desflurane, isoflurane) degradation to various toxic materials. However, desiccation of absorbents with monovalent bases removes this protection. For example, desiccation of soda lime results in a lime that interacts with desflurane and isoflurane to produce carbon monoxide. However, absorbents that contain only $Ca(OH)_2$ as the base may not have this effect. Murray, J. M., et al., *Anesthesiology* (1999) 91:1342-1348.

The invention concerns a particular analog of the above-mentioned anesthetics which is of the formula $CHF_2$—O—$CH(CF_3)_2$. This compound was included in a series of compounds reported by the Terrell group in an article by Speers, L., et al., *J. Med. Chem.* (1971) 14:593-595. According to this article, this compound is a good anesthetic although it appeared to have undesirable side effects in murine models. No report of the solubility of this compound appears in the Speers paper.

DISCLOSURE OF THE INVENTION

It has now been found that the compound of the formula

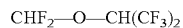
$$CHF_2\text{—}O\text{—}CH(CF_3)_2 \tag{1}$$

has highly favorable solubility properties and can be used successfully as an anesthetic if appropriate means for carbon dioxide removal are employed. Thus, in one aspect, the invention is directed to a method to anesthetize a subject which method comprises administering to said subject by inhalation, a compound of the formula

$$CHF_2\text{—}O\text{—}CH(CF_3)_2 \tag{1}$$

in a regimen wherein said subject inhales the compound of formula (1) and exhales a first gaseous mixture that comprises the compound of formula (1) and carbon dioxide, which first mixture is passed through an absorbent consisting essentially of $Ca(OH)_2$ to obtain a second gaseous mixture essentially lacking carbon dioxide and containing the compound of formula (1), which is re-inhaled by the subject.

In another aspect, the invention is directed to a method to identify an inhaled anesthetic which method comprises passing a candidate anesthetic through an absorbent consisting essentially of $Ca(OH)_2$ under conditions mimicking those used in an anesthetic administration regimen and determining whether said candidate anesthetic is virtually undegraded; whereby a candidate anesthetic that is virtually undegraded is identified as a successful candidate.

MODES OF CARRYING OUT THE INVENTION

One highly desirable property of an inhaled anesthetic is that it permits rapid recovery once the administration of the anesthetic is halted. Typically, during surgical procedures, the subject is continuously administered the anesthetic, and it is helpful if the subject can recover as quickly as possible as soon as administration is stopped. The length of time required for such recovery is a function of the solubility of the anesthetic in the blood, which mimics solubility in the brain. Thus, anesthetics with very low blood/gas partition coefficients are highly desirable. The blood/gas partition coefficient for desflurane is 0.45; for sevoflurane is 0.65 and for isoflurane is even higher. The blood/gas partition coefficient for the compound of formula (1) is only 0.21, making it highly advantageous as permitting more rapid recovery than any of the currently used anesthetics.

Clearly another significant property of an anesthetic is its ability to effect anesthesia in the first place. Desirably, the lower the concentration of the anesthetic in the lung that is required to induce anesthesia the more effective the anesthetic. The minimum alveolar concentration of anesthetic at which 50% of subjects move in response to a noxious stimulus is designated "MAC." In the case of 30-60 year old adult humans, the MAC values are 0.06 atm (i.e., 6%) for desflurane, 0.0115 atm (1.15%) for isoflurane and 0.0185 atm (1.85%) for sevoflurane. An alternative measurement similar to MAC that is based on the righting reflex in mice gave a value for the compound of formula (1) of 0.05 atm (5%). The value obtained in this alternative assay approximates but is usually a bit less than MAC.

Figure 1:
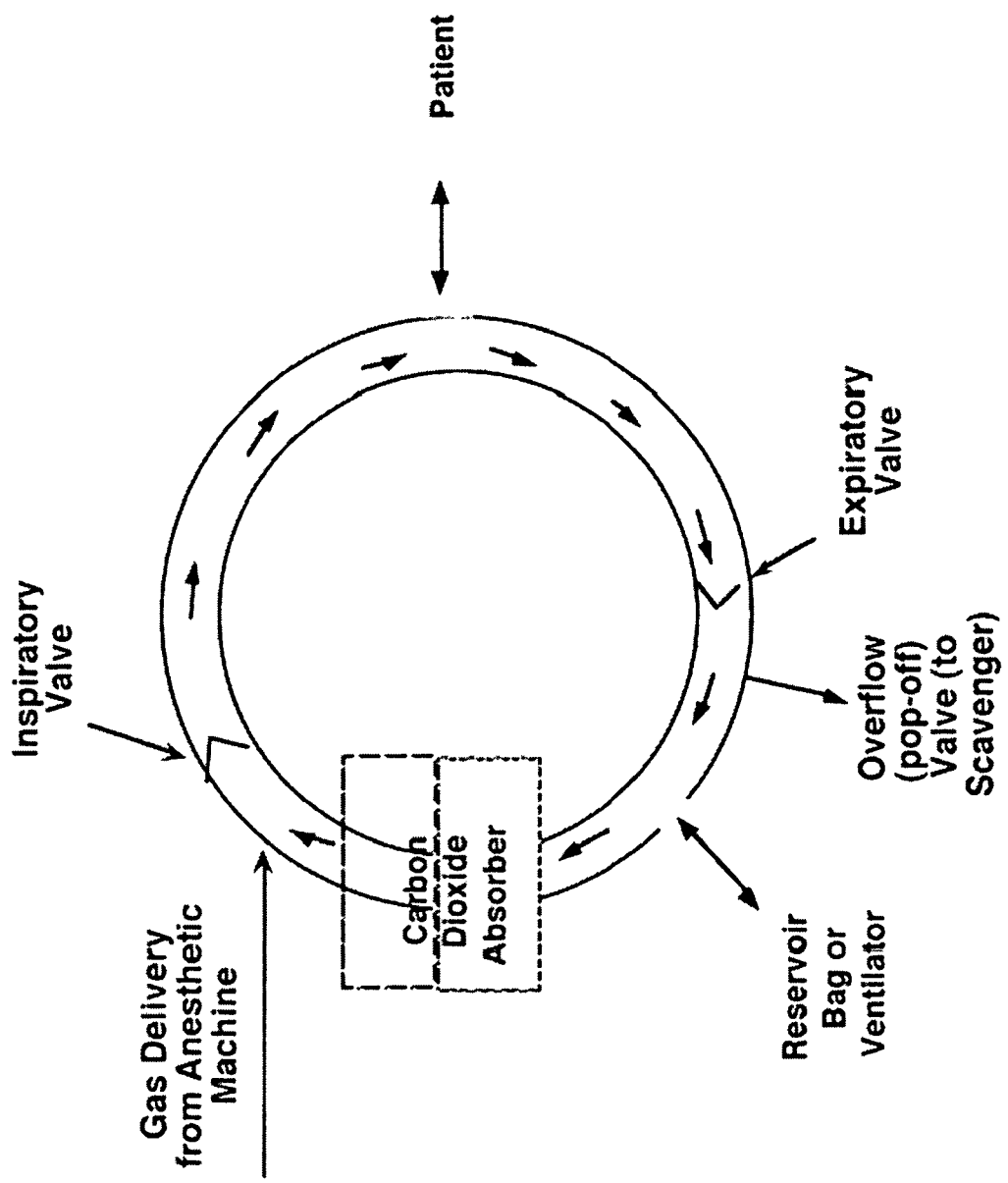
FIG. 1 is a schematic showing the standard method of administering inhaled anesthetics.

The compound of formula (1), however, has a serious drawback for use in the standard system for administering anesthetics because it is rapidly degraded by passage through soda lime under conditions generally encountered in the standard regimen for administration schematically described in FIG. 1. This is in contrast to sevoflurane which degrades only by 13% per hour in soda lime as described by Strum, D. P., et al., *Anesthesiology* (1987) 67:779-781. As shown in the examples below, the degradation of the compound of formula (1) in soda lime is sufficiently dramatic to preclude its use as an anesthetic as a practical matter. However, as demonstrated below, its stability in this regimen using calcium hydroxide in the absence of monovalent bases as the carbon dioxide absorbent results in maintaining the structural integrity of the compound of formula (1). Preferred absorbents (containing only or nearly only calcium hydroxide) also contain sufficient water to prevent the enhanced degradation that occurs in desiccated absorbents. Typically, these absorbents contain roughly 15% by weight of water, but water contents in the range of 1%-20% are acceptable and at least 2-4% water may be present or less than 2% water may be present. Typical amounts are in the range of 10-15% by weight. For soda lime, degradation of isoflurane and sevoflurane increases roughly in proportion to a decrease in water content (Strum, D. P. and Eger, E. I. II: *Anesth Analg* (1994) 78:340-8). Toxic metabolites (e.g., carbon monoxide) do not appear in major amounts with soda lime water contents exceeding 2% (Fang, Z. X., *Anesth Analg* (1995) 80:1187-1193). Only limited and rapidly decreasing degradation of formula (1) by desiccated preferred absorbents occurs (FIG. 4, Table 2), infra and thus it may be assumed that partial dehydration would cause still less degradation.

The subjects to which the invention method is applicable include both human and veterinary subjects such as livestock and pets.

As illustrated in the examples below, evaluating the stability of candidate anesthetics with respect to structural integrity when passed through calcium hydroxide absorbents under conditions simulating those of the regimen shown in FIG. 1 may permit identification of compounds suitable as anesthetics which would otherwise be unacceptable for practical use. As illustrated in the Speers paper referenced above, a number of the compounds that were synthesized have anesthetic qualities, but may degrade unless treated with the milder absorbent calcium hydroxide absent or nearly absent stronger bases.

In that aspect of the invention directed to identifying an inhaled anesthetic by assessing its ability to resist degradation when passed through a carbon dioxide absorbent, successful candidates will undergo virtually no degradation. By "virtually no degradation" or "virtually undegraded" is meant that no more than 3% of the anesthetic is degraded per minute when 10 mg of the candidate anesthetic are contacted with 100 g of an absorbent consisting essentially of calcium hydroxide at a temperature of 40° C. Preferably, no more than 2% is degraded per minute under these conditions and more preferably no more than 1% per minute. It is most preferable that no detectable degradation is shown.

Of course, the candidate anesthetic must have suitable properties in other respects—i.e., being capable of effecting successful anesthesia and showing reasonable recovery times and lacking unacceptable side effects. These additional properties are judged by criteria well known in the art, and are not part of the present invention. The methods of the invention assume that the candidate anesthetic has desirable properties other than being susceptible to degradation in conventional absorbents containing bases other than calcium hydroxide.

The following examples are offered to illustrate but not to limit the invention.

Example 1

Degradation of the Compound of Formula (1) by Soda Lime

Figure 2:
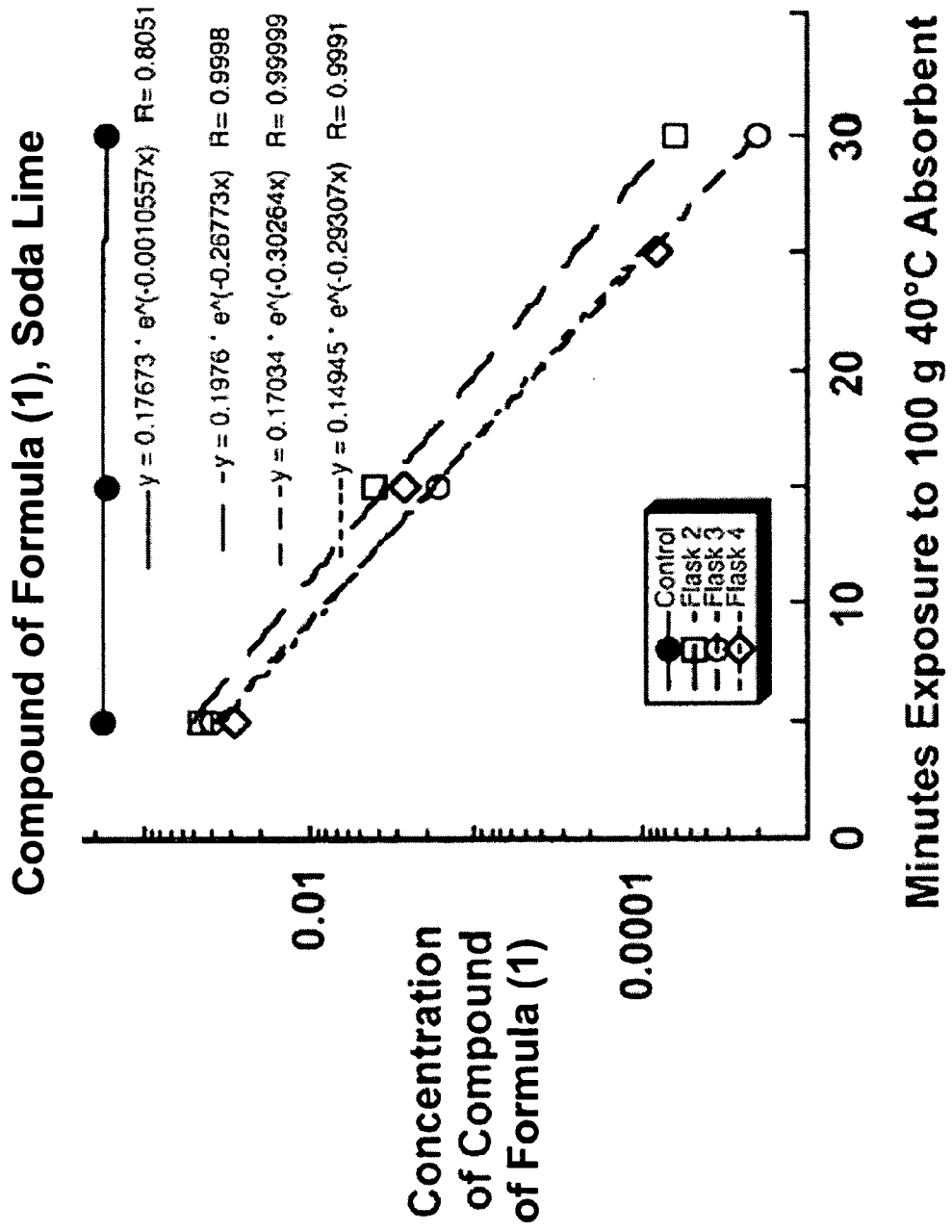
FIG. 2 is a graph showing the degradation of the compound of formula (1) when exposed to wet (normal) soda lime.

Nine milligrams of the compound of formula (1) were placed in each of three 600 ml flasks containing 100 g of soda lime and maintained at 40° C. The 40° C. temperature is chosen to mimic that generated by the exothermic reaction of carbon dioxide with absorbent in a system wherein all gases are rebreathed. Soda lime contains sodium hydroxide as well as approximately 80% calcium hydroxide. A control flask contained the compound of formula (1) but no soda lime. Samples were taken at various timepoints and analyzed by gas chromatography using a flame ionization detector. The results are shown in FIG. 2. The control showed no degradation, but the flasks containing soda lime resulted in essentially complete degradation after 30 min. It will be noted that the Y-axis is on a log scale so that the depletion is quite dramatic.

Example 2

Treatment with Calcium Hydroxide (Amsorb™)

Figure 3:
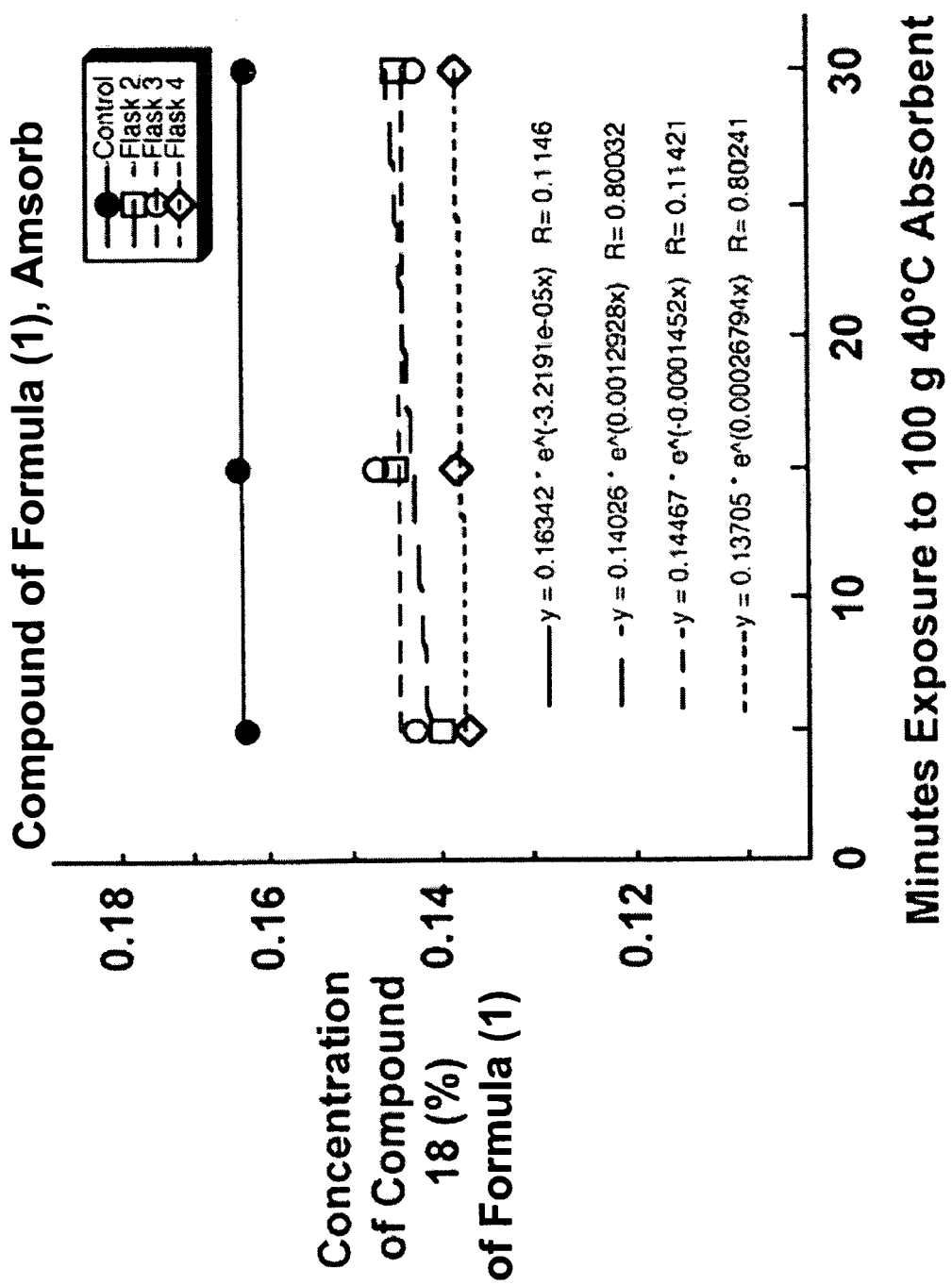
FIG. 3 is a graph showing the lack of degradation of the compound of formula (1) when exposed to a carbon dioxide absorbent composed of wet (normal) calcium hydroxide (Amsorb®) but no other bases

The procedure was identical to that of Example 1 except that an absorbent containing only calcium hydroxide as the base was used. This absorbent is marketed under the trademark Amsorb®. Amsorb® was substituted in the procedure of Example 1 for soda lime in the three test flasks The results are shown in FIG. 3. As demonstrated, the percentage of the compound of formula (1) in the flask remained constant over the same 30 min. interval under the same conditions as those in Example 1.

Example 3

Additional Absorbents

The dramatic decrease in degradation with substitution of Amsorb® for soda lime applies to other absorbents that are composed of calcium hydroxide but contain minimal or no monovalent bases, LoFloSorb® and Drägersorb® Free. The general procedure of Example 1 was repeated using these two commercially available absorbents. The data in Table 1 indicate that the three absorbents either do not degrade the compound of formula (1) or sevoflurane [$CH_2F-O-CH(CF_3)_2$] or cause only a miniscule degradation that could not be accurately measured. All studies were conducted at 40° C. In all cases, the absorbents were "wet" (contained approximately 15% water by weight). The data in the table were obtained using the protocol set forth above wherein 100 g of absorbent was placed in a 600 mL flask, and 100 mL of anesthetic at the indicated concentration was inserted. Each study was done in triplicate. A minus sign before the value for "% degraded per minute" indicates that a slight increase in concentration occurred over the period of study. Values for % degraded per minute are given as the average and standard deviation (SD).

TABLE 1

Degradation Rates Associated with Specific Absorbents.

| Absorbent | Anesthetic | % Injected | % Degraded per Minute | SD |
|---|---|---|---|---|
| Soda Lime | Formula (1) | 1.00 | 25.0 | 1.3 |
| Amsorb ® | Formula (1) | 1.00 | −0.05 | 0.07 |
| LoFloSorb ® | Formula (1) | 1.00 | 0.2 | 0.2 |
| Drägersorb ® Free | Formula (1) | 1.00 | 0.102 | 0.018 |
| Drägersorb ® Free | Sevoflurane | 1.84 | −0.058 | 0.039 |

Example 4

Effect of Desiccation

Previous studies found that the presence of water in the absorbent prevents or minimizes the degradation of isoflurane and desflurane (Eger, E. I., II, and Strum, D. P., *Anesth Analg* (1987) 66:1312-1315). Some of the above studies of degradation were repeated with dry absorbent.

Drying was accomplished by placing wet absorbent in a large flask receiving 1-1.5 L/min of oxygen (dry; no water vapor) for 4 days. The flask rested in an incubator at 50° C. The absorbent contained in the flask was weighed repeatedly (to essentially constant weight loss). The original water content for the three absorbents (i.e., the weight lost) was: Amsorb® 14.1%; Drägersorb® Free 18.9%; and LoFloSorb® 14.3%.

As above, all studies were conducted at 40° C. Desiccated (dry) absorbent (grams indicated) was placed in a 600 mL flask, and 100 or 200 mL of anesthetic at the indicated concentration was inserted. A minus sign before the value for % degraded per minute indicates that a slight increase in concentration occurred over the period of study. Values for % degraded per minute are given as the average and standard deviation (SD). The results are shown in Table 2.

TABLE 2

Degradation by Desiccated ("Dry") Absorbents

| Absorbent | N | Grams Absorbent | Anesthetic | % Anesthetic Inj | mL Inj | % Degr Per min | SD |
|---|---|---|---|---|---|---|---|
| Amsorb ® | 3 | 20 | Formula (1) | 1.00 | 100 | 0.7 | 0.3 |
| Amsorb ® | 3 | 100 | Formula (1) | 1.00 | 100 | 2.7 | 0.3 |
| Amsorb ® | 2 | 50 | Desflurane | 4.20 | 100 | −0.1 | 0.1 |
| Amsorb ® | 3 | 100 | Sevoflurane | 1.84 | 100 | 5.01 | 0.90 |
| LoFloSorb ® | 3 | 25 | Formula (1) | 1.00 | 100 | 55.0 | 4.4 |
| LoFloSorb ® | 3 | 50 | Formula (1) | 1.00 | 200 | 40.7 | 8.0 |
| LoFloSorb ® | 3 | 50 | Desflurane | 4.20 | 200 | 0.5 | 0.3 |
| LoFloSorb ® | 3 | 25 | Sevoflurane | 1.84 | 100 | 38.5 | 2.8 |
| Drägersorb ® Free | 3 | 25 | Formula (1) | 1.00 | 100 | 0.28 | 0.11 |
| Drägersorb ® Free | 3 | 25 | Sevoflurane | 1.84 | 100 | 0.52 | 0.14 |

Table 2 shows that although wet absorbent did not appreciably degrade the compound of formula (1) or sevoflurane (Table 1), the dry absorbents could degrade these anesthetics and differed in their capacity to cause degradation. Dry Drägersorb® Free was most benign, causing little or no degradation. Dry Amsorb® caused a small amount of degradation of the compound of formula (1) and sevoflurane, but none of desflurane. Dry LoFloSorb® caused a large rate of degradation of both the compound of formula (1) and sevoflurane, but not desflurane ($CHF_2-O-CHFCF_3$). Unlike Amsorb® and Drägersorb® Free, LoFloSorb® may contain a small amount of sodium hydroxide (thus explaining the degradation in desiccated absorbent).

Thus, even desiccation of some absorbents does not increase the risks of degradation and of production of toxic degradation products, and the degradation behavior of the compound of formula (1), does not differ from that of the accepted clinical anesthetic sevoflurane.

Example 5

Effect of Additional Anesthetic

Figure 4:
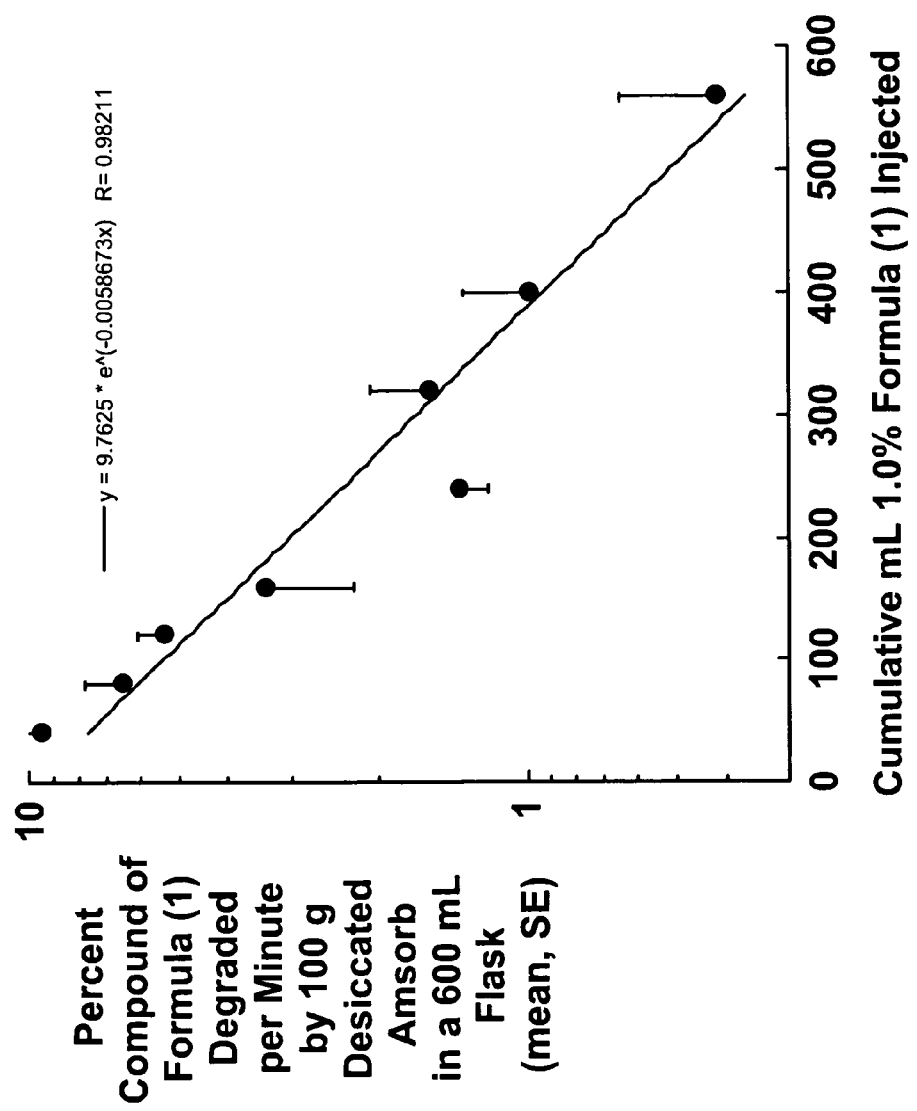
FIG. 4 is a graph showing the decrease in degradation of the compound of formula (1) with repeated application of formula (1) to a desiccated absorbent composed solely of calcium hydroxide (Amsorb®). This result probably reflects progressive saturation of degradation sites.

To determine whether the degradation of the compound of formula (1) seen with dry Amsorb® is limited by the amount of anesthetic to which the dry Amsorb® was exposed, the compound of formula (1) was repeatedly added to three flasks, each time determining the rate of degradation after each addition of further anesthetic. The rate of degradation progressively decreased as more compound of formula (1) was added (FIG. 4).

Thus, used under the conditions of those during surgery, the sites available for degradation become saturated.

Example 6

Effectiveness of Formula (1) as an Anesthetic

In a closed system employing Amsorb® as the absorbent, four mice were anesthetized using the compound of formula (1). The righting reflex was lost at 3.22±0.54% of formula (1). The rectal temperature of the mice at the end of this experiment was 30° C. which is hypothermic for mice. Hypothermia decreases anesthetic requirement (Eger, E. I. II and Johnson, B. H.; *Anesth Analg* (1987) 66:974-976), and thus this experiment probably underestimated the concentration producing the loss of righting reflex.

In an additional experiment, conducted at 37° C. which is normothermic, five rats were anesthetized using the compound of formula (1) and the MAC value found was 8.34±0.84%.

In neither of these cases was there irritation of the central nervous system, and recovery was rapid—the animals were awake within 2-3 minutes after administration of the anesthetic was stopped.

All survived for 24 hours in apparent good health.

The invention claimed is:

1. A method to anesthetize a subject which method comprises administering to said subject by inhalation, a compound of the formula $$CHF_2\text{—}O\text{—}CH(CF_3)_2 \quad (1)$$

in a regimen wherein said subject inhales the compound of formula (1) and exhales a first gaseous mixture that comprises the compound of formula (1) and carbon dioxide, which first gaseous mixture is passed through an absorbent composition wherein the absorbent consists essentially of $Ca(OH)_2$ to obtain a second gaseous mixture depleted in carbon dioxide and containing the compound of formula (1), which second gaseous mixture is re-inhaled by the subject.

2. The method of claim 1 wherein the absorbent composition comprises 5-15% water.

3. The method of claim 1 wherein the absorbent composition comprises less than 2% water.

4. The method of claim 1 wherein the subject is human.

5. The method of claim 1 wherein the subject is a veterinary subject.

6. A method to identify an inhaled anesthetic compound that can be recycled when in use to anesthetize a subject which method comprises passing a candidate anesthetic through an absorbent composition wherein the absorbent consists essentially of $Ca(OH)_2$ under conditions mimicking those used in an inhaled anesthetic administration regimen and determining whether said candidate anesthetic is degraded;

whereby a candidate anesthetic that is virtually not degraded is identified as a successful candidate.

7. The method of claim 6 wherein the absorbent composition comprises 5-15% water.

8. The method of claim 6 wherein the absorbent composition comprises less than 2% water.

* * * * *